United States Patent
Chassot et al.

(10) Patent No.: US 7,122,061 B2
(45) Date of Patent: Oct. 17, 2006

(54) AGENTS FOR DYEING KERATIN FIBERS, CONTAINING 4-AMINOBIPHENYL-3-OL-DERIVATIVES

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 10/501,833

(22) PCT Filed: May 13, 2003

(86) PCT No.: PCT/EP03/04960

§ 371 (c)(1), (2), (4) Date: Mar. 21, 2005

(87) PCT Pub. No.: WO2004/041226

PCT Pub. Date: May 21, 2004

(65) Prior Publication Data

US 2005/0155160 A1    Jul. 21, 2005

(30) Foreign Application Priority Data

Nov. 2, 2002  (DE) ................................ 102 51 106

(51) Int. Cl.
*A61K 7/13* (2006.01)
(52) U.S. Cl. ...................... 8/405; 8/409; 8/411; 8/412; 548/400; 549/415; 549/476; 549/478; 549/479; 549/480; 549/497
(58) Field of Classification Search .............. 8/405, 8/409, 411, 412; 548/400; 549/415, 476, 549/478, 479, 480, 497
See application file for complete search history.

(56) References Cited

U.S. PATENT DOCUMENTS

| 3,577,411 | A | 5/1971 | Guglielmetti | 260/240 |
|---|---|---|---|---|
| 4,396,392 | A | 8/1983 | Konrad et al. | 8/412 |
| 6,262,113 | B1 | 7/2001 | Hertzberg | 514/522 |
| 6,380,235 | B1 | 4/2002 | Bender | 514/395 |
| 2004/0200010 | A1* | 10/2004 | Pasquier et al. | 8/405 |

FOREIGN PATENT DOCUMENTS

| DE | 28 33 989 |  | 2/1980 |
| DE | 101 41 722 A |  | 3/2003 |

OTHER PUBLICATIONS

Bradshaw. L.: "The Metabolsim of the Carcinogen . . . " Acta Unio Internationalis Contra Cancrum, BD. 15, 1959, pp. 137-141.
Laham, S., et al: "Identification of Bladder Carcinogens by . . . " Industrial Medicine, BD. 39, NR. 3, 1970, pp. 142-147.

* cited by examiner

Primary Examiner—Eisa Elhilo
(74) Attorney, Agent, or Firm—Michael J. Striker

(57) ABSTRACT

The present invention has for an object compounds of formula (I) and colorants containing these 4-aminobiphenyl-3-ol derivatives of general formula (I) for dyeing keratin fibers, particularly hair,

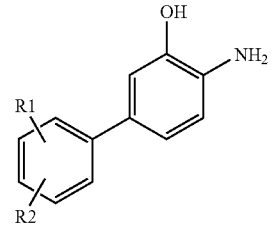

(I)

wherein
R1 and R2 independently of each other denote hydrogen, a halogen atom, a cyano group, a hydroxyl group, a $C_1$–$C_4$-alkoxy group, a $C_2$–$C_4$-hydroxyalkoxy group, a $C_1$–$C_6$-alkyl group, a nitro group, a trifluoromethyl group, a —C(O)H group, a —C(O)CH$_3$ group, a —C(O)CF$_3$ group, an —Si(CH$_3$)$_3$ group or a $C_1$–$_6$-hydroxyalkyl group or R1 and R2 together form an —O—CH$_2$—O— bridge.

9 Claims, No Drawings

AGENTS FOR DYEING KERATIN FIBERS, CONTAINING 4-AMINOBIPHENYL-3-OL-DERIVATIVES

BACKGROUND OF THE INVENTION

The present invention has for an object colorants for oxidative dyeing of keratin fibers, particularly human hair, containing 4-aminobiphenyl-3-ol derivatives.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diamino-1-(2-hydroxyethyl)pyrazole, and suitable couplers are, for example, resorcinol, 2-methyl-resorcinol, 1-naphthol, 3-aminophenol, m-phenylenediamine, 2-amino-4-(2'-hydroxyethyl)amino-anisole, 1,3-diamino-4-(2'-hydroxyethoxy)benzene and 2,4-diamino-5-fluorotoluene.

The oxidation dyes used for dyeing human hair must meet numerous requirements in addition to producing hair colorations that are stable for at least 4 to 6 weeks. For example, these dyes must be harmless from a toxicological and dermatological standpoint, and the hair colorations obtained must have good light fastness, resistance to permanent waving, rubbing fastness and resistance to shampooing as well as sufficient resistance to perspiration. Moreover, by combining appropriate developers and couplers, it must be possible to create a wide range of different color shades.

The adjustment of lighter color shades presents a special problem in terms of uniform dye uptake from the hair roots to the hair tips and in terms of resistance of the colorations to permanent wave treatment. The use of direct yellow-dyeing aromatic nitro dyes together with oxidative hair dye precursors represents a partial solution of the said problem, but the stability of the colorations over a period of several weeks is often unsatisfactory.

SUMMARY OF THE INVENTION

To solve the said problem, German Unexamined Patent Application 28 33 989 proposes the use of 6-amino-3-methylphenol as a yellow-dyeing oxidative dye in oxidative hair colorants. Although this compound is well suited as shade-adjustment agent for the creation of bright blond shades and gold shades, it does not fully meet requirements, particularly as regards the resistance of the hair colorations to the action of permanent wave agents.

We have now found that certain 4-aminobiphenyl-3-ol derivatives of general formula (I) meet to an unusually high degree the requirements placed on dye components. In fact, the use of these 4-aminobiphenyl-3-ol derivatives in an oxidizing medium produces color shades that are unusually wash-fast and resistant to permanent waving.

The object of the present invention is therefore a colorant for oxidative dyeing of keratin fibers, characterized in fiat it contains at least one 4-aminobiphenyl-3-ol derivative of general formula (I) or a physiologically compatible, water-soluble salt thereof.

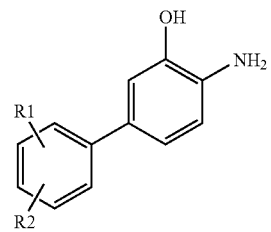

wherein R1 and R2 independently of each other denote hydrogen, a halogen atom, a cyano group, a hydroxyl group, a $C_1$–$C_4$-alkoxy group, a $C_2$–$C_4$-hydroxyalkoxy group, a $C_1$–$C_6$-alkyl group, a nitro group, a trifluoromethyl group, a —C(O)H group, a —C(O)CH$_3$ group, a —C(O)CF$_3$ group, an —Si(CH$_3$)$_3$ group or a $C_1$–$C_6$-hydroxyalkyl group, or R1 and R2 together form an —O—CH$_2$—O— bridge.

Suitable compounds of formula (I) are, for example, the following compounds: 4-aminobiphenyl-3-ol, 4-amino-2'-chlorobiphenyl-3-ol, 4-amino-2'-cyanobiphenyl-3-ol, 4-amino-2'-fluorobiphenyl-3-ol, 4-amino-2'-methylbiphenyl-3-ol, 4-amino-2'-trifluoromethylbiphenyl-3-ol, 4-amino-3'-chlorobiphenyl-3-ol, 4-amino-3'-cyanobiphenyl-3-ol, 4-amino-3'-fluorobiphenyl-3-ol, 4-amino-3'-methylbiphenyl-3-ol, 4-amino-3'-trifluoromethylbiphenyl-3-ol, 4-amino-4'-chlorobiphenyl-3-ol, 4-amino-4'-cyanobiphenyl-3-ol, 4-amino-4'-fluorobiphenyl-3-ol, 4-amino-4'-methylbiphenyl-3-ol, 4-amino-4'-trifluoromethylbiphenyl-3-ol, 4-amino-2',3'-dichlorobiphenyl-3-ol, 4-amino-2'-chloro-3'-fluorobiphenyl-3-ol, 4-amino-2'-chloro-3'-methylbiphenyl-3-ol 4-amino-2'-chloro-5'-chlorobiphenyl-3-ol, 4-amino-2'-chloro-5'-fluorobiphenyl-3-ol, 4-amino-2'-chloro-5'-methylbiphenyl-3-ol, 4-amino-2',6'-dichlorobiphenyl-3-ol, 4-amino-2'-chloro-6'-fluorobiphenyl-3-ol, 4-amino-2'-chloro-6'-methylbiphenyl-3-ol, 4-amino-2'-fluoro-3'-chlorobiphenyl-3-ol, 4-amino-2'-fluoro-3'-fluorobiphenyl-3-ol, 4-amino-2'-fluoro-3'-methylbiphenyl-3-ol, 4-amino-2'-fluoro-5'-chlorobiphenyl-3-ol, 4-amino-2',5'-difluorobiphenyl-3-ol, 4-amino-2'-fluoro-5'-methylbiphenyl-3-ol, 4-amino-2'-fluoro-6'-chlorobiphenyl-3-ol, 4-amino-2',6'-difluorobiphenyl-3-ol, 4-amino-2'-fluoro-6'-methylbiphenyl-3-ol, 4-amino-2'-methyl-3'-fluorobiphenyl-3-ol, 4-amino-2',3'-dimethylbiphenyl-3-ol, 4-amino-2'-methyl-5'-chlorobiphenyl-3-ol, 4-amino-2'-methyl-5'-fluorobiphenyl-3-3-ol, 4-amino-2'-methyl-6'-chlorobiphenyl-3-ol, 4-amino-2'-methyl-6'-fluorobiphenyl-3-ol, 4-amino-2',6'-dimethylbiphenyl-3-ol, 4-amino-3'-chloro-5'-chlorobiphenyl-3-ol, 4-amino-3'-chloro-5'-fluorobiphenyl-3-ol, 4-amino-3'-chloro-5'-methylbiphenyl-3-ol, 4-amino-3'-fluoro-5'-chlorobiphenyl-3-ol, 4-amino-3',5'-difluorobiphenyl-3-ol, 4-amino-3'-fluoro-5'-methylbiphenyl-3-ol, 4-amino-3'-methyl-5'-chlorobiphenyl-3-ol, 4-amino-3'-methyl-5'-fluorobiphenyl-3-ol, 4-amino-3',5'-dimethylbiphenyl-3-ol, 4-amino-3',4'-dichlorobiphenyl-3-ol, 4-amino-3'-chloro-4'-fluorobiphenyl-3-ol, 4-amino-3'-chloro-4'-methylbiphenyl-3-ol, 4-amino-4',6'-dichlorobiphenyl-3-ol, 4-amino-4'-chloro-6'-fluorobiphenyl-3-ol, 4-amino-4'-chloro-6'-methylbiphenyl-3-ol, 4-amino-3'-fluoro-4'-chlorobiphenyl-3-ol, 4-amino-3',4'-difluorobiphenyl-3-ol, 4-amino-3'-fluoro-4'-methylbiphenyl-3-ol, 4-amino-4'-fluoro-6'-chlorobiphenyl-3-ol, 4-amino-4'-6'-fluorobiphenyl-3-ol, 4-amino-4'-fluoro-6'-methylbiphenyl-3-ol, 4-amino-3'-methyl-4'-chlorobiphenyl-3-ol 4-amino-3'-methyl-4'-fluorobiphenyl- 3-ol, 4-amino-3',4'-dimethylbiphenyl-3-ol, 4-amino-4'-methyl-6'-chlorobiphenyl-3-ol, 4-amino-4'-methyl-6'-fluorobiphenyl-3-ol, 4-amino-4',6'-dimethylbiphenyl-3-ol, 2-amino-5-benzo[1,3]dioxo-5-ylphenol and the physiologically compatible salts thereof.

Preferred compounds of formula (I) are those wherein (i) R1 denotes hydrogen and/or (ii) R2 denotes hydrogen, a methyl group, a trifluoromethyl group, a fluorine atom or a chlorine atom.

Particularly preferred are the following compounds of formula (I): 4-aminobiphenyl-3-ol, 4-amino-2'-chlorobiphenyl-3-ol, 4-amino-3'-chlorobiphenyl-3-ol, 4-amino-4'-chlorobiphenyl-3-ol, 4-amino-2'-fluorobiphenyl-3-ol, 4-amino-3'-fluorobiphenyl-3-ol, 4-amino-4'-fluorobiphenyl-3-ol and the physiologically compatible salts thereof.

The 4-aminobiphenyl-3-ol derivatives of formula (I) of the invention can be prepared by known methods of synthesis, for example by the palladium(0)-catalyzed coupling of a substituted benzene of formula (II)

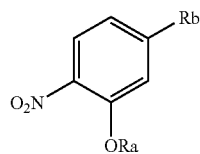

(II)

with a compound of formula (III)

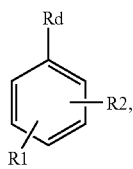

(III)

wherein

Rb denotes a halogen atom and Rd denotes $B(OH)_2$ or Rb denotes $B(OH)_2$ and Rd stands for a halogen atom, Ra stands for a protective group as described, for example, in the chapter on "Protective Groups" in Organic Synthesis, chapter 3, Wiley Interscience, 1991, and R1 and R2 have the same meaning as in formula (I);

followed by reduction and elimination of the protective group.

The compounds of formula (I) of the invention give colorations of excellent color stability, in particular in terms of wash fastness, rubbing fastness and resistance to permanent waving.

The colorant of the invention contains the 4-aminobiphenyl-3-ol derivative of formula (I) in an amount from about 0.001 to 5 weight percent, an amount from about 0.005 to 2 weight percent and particularly from 0.01 to 1 weight percent being preferred.

The compounds of formula (I) dye keratin fibers, particularly human hair, to yellow shades without the addition of other dyes.

To achieve other color shades, one or more common oxidative dyes, for example developers or couplers, alone or in admixture with one another, may be added.

Suitable couplers are, in particular, N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 1,3-diamino-4-(2,3-dihydroxypropoxy)benzene, 1,3-diamino-4-(3-hydroxypropoxy)benzene, 1,3-diamino-4-(2-methoxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)-amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxy-phenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylene-dioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Preferred developers are 1,4-diaminobenzene (p-phenylenediamine), 1,4-diamino-2-methylbenzene (p-toluylenediamine), 1,4-diamino-2,6-diethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 4-(2,5-diaminophenyl)-2-[(diethylamino)methyl]thiophene, 2-chloro-3-(2,5-diaminophenyl)thiophene, 1,4-diamino-2-(pyridin-3-yl)benzene, 2,5-diaminobiphenyl, 2,5-diamino-4'-(1-methylethyl)-1,1'-biphenyl, 2,3',5-triamino-1,1'-biphenyl, 1,4-diamino-2-methoxymethylbenzene, 1,4-diamino-2-aminomethylbenzene, 1,4-diamino-2-[(phenylamino)methyl]benzene, 1,4-diamino-2-{[ethyl-(2-hydroxyethyl)amino]methyl}benzene, 1,4-diamino-2-hydroxymethylbenzene, 1,4-diamino-2-(2-hydroxyethoxy)benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 4-{[(4-aminophenyl)methyl]amino}aniline, 4-[(4-aminophenylamino)methyl]phenol, 1,4-diamino-N-(4-pyrrolidin-1-ylbenzyl)benzene, 1,4-diamino-N-furan-3-ylmethylbenzene, 1,4-diamino-N-thiophen-2-ylmethylbenzene, 1,4-diamino-N-furan-2-ylmethylbenzene, 1,4-diamino-N-thiophen-3-yl-methylbenzene, 1,4-diamino-N-benzylbenzene, 1,4-diamino-2-(1-hydroxyethyl)benzene, 1,4-diamino-2-(2-hydroxyethyl)benzene, 1,4-diamino-2-(1-methylethyl)benzene, 1,3-bis[(4-amino-phenyl)(2-hydroxyethyl)amino]-2-propanol, 1,4-bis[(4-aminophenyl)amino]butane, 1,8-bis(2,5-diaminophenoxy)-3,6-dioxaoctane, 2,5-diamino-4'-hydroxy-1,1'-biphenyl, 2,5-diamino-2'-trifluoromethyl-1,1'-biphenyl, 2,4',5-triamino-1,1'-biphenyl, 4-aminophenol, 4-amino-3-methylphenol, 4-amino-3-(hydroxymethyl)phenol, 4-amino-3-fluorophenol, 4-methylaminophenol, 4-amino-2-(aminomethyl)-phenol, 4-amino-2-(hydroxymethyl)phenol, 4-amino-2-fluorophenol, 4-amino-2-[(2-hydroxyethyl)-amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-1-pentyl-1H-pyrazole, 4,5-diamino-1-(phenylmethyl)-1H-pyrazole, 4,5-diamino-1-[(4-methoxyphenyl)-methyl-1H-pyrazole, 2-aminophenol, 2-amino-6-methylphenol, 2-amino-5-methylphenol, 1,2,4-trihydroxybenzene, 2,4-diaminophenol, 1,4-dihydroxybenzene and 2-{[(4-aminophenyl)amino]-methyl}-1,4-diaminobenzene.

The aforesaid developers and couplers are present in the colorant of the invention in a total amount of about 0.01 to 12 weight percent and particularly about 0.2 to 6 weight percent.

Moreover, the colorant of the invention can contain other dye components, for example 4-(2,5-diaminobenzylamino) aniline or 3-(2,5-diaminobenzylamino)aniline, as well as common natural dyes, dyes identical to natural ones, or synthetic direct dyes from the group consisting of anionic (acid) and cationic (basic) dyes, triarylmethane dyes, nitro dyes, disperse dyes and azo dyes., for example natural dyes such as indigo or henna, triphenylmethane dyes such as 4-[(4'-aminophenyl)-(4'-imino-2'',5''-cyclohexadien-1''-ylidene)methyl]-2-methylaminobenzene monohydrochloride (C.I. 42 510), and 4-[(4'-amino-3'-methylphenyl)-(4''-imino-3''-methyl-2'',5''-cyclohexadien-1''-ylidene)-methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl)aminonitrobenzene, 2-chloro-6-(ethylamino)4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)-amino-4-nitrobenzene, azo dyes such as sodium 6-[(4'-aminophenyl)azo]-5-hydroxynaphthalene-1-sulfonate (C.I. 14 805) and disperse dyes, for example 1,5-diaminoanthraquinone and 1,4,5,8-tetraaminoanthraquinone.

The colorant can contain the aforesaid other dye components in a total amount of about 0.1 to 4 weight percent.

The aforesaid developers and/or couplers and/or other dye components in combination with the compounds of formula (I) of the invention make it possible to obtain many different color shades. For example, blond to brown hair colorations can be achieved by use of a combination of the compounds of formula (I) and 4-(2,5-diaminobenzylamino)aniline.

Naturally, the couplers, developers and other dye components, provided they are bases, can also be used in the form of their physiologically compatible salts of organic or inorganic acids, for example hydrochloric acid or sulfuric acid, or—if they contain aromatic OH— groups—in the form of salts of bases, for example as alkali metal phenoxides.

Moreover, if the colorants are to be used for dyeing hair, they can also contain common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be formulated, for example, as a solution, particularly an aqueous or aqueous-alcoholic solution, or as a paste, cream, gel, emulsion or aerosol preparation. Such a colorant formulation consists of a mixture of dye components and additives commonly used for such formulations.

Common additives to solutions, creams, emulsions or gels are, for example, solvents such as water, lower aliphatic alcohols, for example ethanol, propanol or isopropanol, glycerol or glycols such as 1,2-propylene glycol; moreover wetting agents or emulsifiers from the classes of anionic, cationic, amphoteric or nonionic surface-active substances such as, for example, the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides and ethoxylated fatty esters, furthermore thickeners such as the higher fatty alcohols, starch, cellulose derivatives, petrolatum, paraffin oil and fatty acids; moreover hair-care agents such as cationic resins, lanolin derivatives, cholesterol, pantothenic acid and betaine. The said constituents are used in amounts commonly employed for such purposes, for example the wetting agents and emulsifiers at a concentration from about 0.5 to 30 weight percent, the thickeners in an amount from about 0.1 to 30 weight percent and the hair-care agents at a concentration from about 0.1 to 5 weight percent.

Depending on the composition, the colorant of the invention can be weakly acidic, neutral or alkaline. In particular, it has a pH from 6.5 to 11.5, the adjustment to a basic value preferably being achieved with ammonia or an organic amine, for example with monoethanolamine or triethanolamine, or an amino acid, or an inorganic base such as sodium hydroxide or potassium hydroxide. It is also possible to use combinations of the aforesaid compounds, particularly a combination of ammonia and monoethanolamine. For pH adjustment in the acidic range, an inorganic or organic acid, for example phosphoric acid, acetic acid, citric acid or tartaric acid, can be used.

For use in oxidative dyeing of hair, the afore-described colorant is mixed with an oxidant just before use and the resulting mixture is applied to the hair in an amount sufficient for the hair treatment, in general from about 60 to 200 grams, depending on the fullness of the hair.

Suitable oxidants for developing the hair coloration are mainly hydrogen peroxide or the compounds of addition thereof to urea, melamine, sodium borate or sodium carbonate in the form of a 3 to 12%, preferably 6% aqueous solution. Atmospheric oxygen can also be used. If a 6% hydrogen peroxide solution is used as oxidant, the weight ratio of hair colorant to oxidant is from 5:1 to 1:2 and preferably 1:1. Larger amounts of oxidant are used primarily at higher dye concentrations in the hair colorant or when more pronounced hair bleaching is wanted at the same time. The mixture is allowed to act on the hair at 15 to 50° C. for about 10 to 45 minutes, preferably for 30 minutes, after which the hair is rinsed with water and dried. Optionally, following this rinsing the hair is washed with a shampoo and optionally post-rinsed with a weak organic acid, for example citric acid or tartaric acid. The hair is then dried.

The colorant of the invention containing a 4-aminobiphenyl-3-ol derivative of formula (I) gives colorations of excellent color stability, particularly in terms of light fastness, wash fastness, rubbing fastness and resistance to permanent waving. As far as the coloring properties are concerned, depending on the kind and composition of the dye components, the colorants of the invention provide a wide range of different color shades ranging from blond to brown, purple, violet, blue and black. Said shades are characterized by unusually high color intensity and good color balancing between damaged and undamaged hair. Furthermore, the very good coloring properties of the hair colorants of the present patent application are, in particular, characterized by the fact that these colorants also make it possible to dye gray, chemically not previously damaged hair with good covering power and without any problems.

Another object of the present invention are 4-aminobiphenyl-3-ol derivatives of formula (I) among which 4-aminobiphenyl-3-ol, 4-amino-2'-chlorobiphenyl-3-ol, 4-amino-3'-chlorobiphenyl-3-ol, 4-amino-4'-chlorobiphenyl-3-ol, 4-amino-2'-fluorobiphenyl-3-ol, 4-amino-3'-fluorobiphenyl-3-ol and 4-amino-4'-fluorobiphenyl-3-ol and the physiologically compatible salts thereof are particularly preferred.

The following examples will explain the subject matter of the invention in greater detail without limiting its scope.

EXAMPLES

Example 1

Synthesis of 4-amino-1,1'-biphenyl-3-ol

A. Synthesis of 4-chloro-2-(ethoxymethoxy)-1-nitrobenzene 10 g (230 mmol) of a sodium hydride dispersion (55% in oil) was added intermittently to a solution of 26 g (150 mmol) of 3-chloro-2-hydroxynitrobenzene in 280 mL of acetonitrile at 0° C. The mixture was allowed to agitate for 50 min at 0° C. Then, 18.4 g (185 mmol) of chloromethyl ethyl ether was added, and the mixture was allowed to agitate 1 hour at 0° C. The reaction mixture was then poured onto ice and extracted with ethyl acetate, and the organic phase was washed with a saturated aqueous sodium chloride solution, dried over $Na_2SO_4$ and filtered and the filtrate was evaporated. This gave 37 g of 4-chloro-2-(ethoxymethoxy)-1-nitrobenzene.

$^1$-NMR (300 MHz, DMSO-D6): δ=7.95 (d, 1H), 7.16 (dd, 1H), 7.55 (d, 1H), 7.24 (dd, 1H), 5.47 (s, 2H), 3.707 (q, 2H), 1.14 (t, 3H).

B. Synthesis of 4-nitro-1,1'-biphenyl-3-ol 9.3 g (40 mmol) of 4-chloro-2-(ethoxymethoxy)-1-nitrobenzene from step A and 7.3 g (60 mmol) of phenylboric acid were dissolved in 170 mL of toluene under nitrogen. Then, 0.1 g (0.5 mmol) of palladium acetate, 0.35 g (1 mmol) of 2-(dicyclohexylphosphino)biphenyl and 15 g of tripotassium phosphate were added, and the reaction mixture was heated to 80° C. At the end of the reaction, the reaction mixture was poured into 100 mL of ethyl acetate and the organic phase was extracted with dilute sodium hydroxide solution and then dried over magnesium sulfate. The solvent was distilled off in a rotary evaporator, and the residue was purified on silica gel with hexane/ethyl acetate (9:1). The resulting product dissolved in 50 mL of ethanol was heated to 50° C. 80 mL of a 2.9-molar ethanolic hydrochloric acid solution was then added dropwise after which the reaction mixture was cooled to 0° C. The precipitate was filtered off, washed twice with 20-mL portions of ethanol and then dried. This gave 9.35 g of 4-nitro-1,1'-biphenyl-3-ol.

1H-NMR (300 MHz, DMSO-D6): δ=11.08 (s, 1H), 8.0 (d, 1H), 7.7 (m, 2H), 7.5 (m, 3H), 7.39(d, 1H), 7.30 (dd, 1H).

C. Synthesis of 4-amino-1,1'-biphenyl-3-ol 8.8 g (40 mmol) of 4-nitro-1,1'-biphenyl-3-ol from step B was dissolved in 120 mL of ethanol and hydrogenated in the presence of 0.8 g of a palladium-activated carbon catalyst (10%) at 25° C. After the required quantity of hydrogen had been absorbed, the catalyst was filtered off, and the solvent was distilled off in a rotary evaporator. This gave 7.3 g of 4° amino-1,1'-biphenyl-3-ol.

$^1$H-NMR: (300 Mz, DMSO-D6): δ=9.15 (s, 1H), 7.49 (m, 2H), 7.37 (m, 2H), 7.27 (t, 1H), 6.96 (d, 1H), 6.89 (dd, 1H), 6.7 (d, 1H).

Example 2

Synthesis of 4-amino-2'-chloro[1,1'biphenyl]-3-ol

A. Synthesis of 4-nitro-2'-chloro[1,1'-biphenyl]-3-ol 9.3 g (40 mmol) of 4-chloro-2-(ethoxymethoxy)-1-nitrobenzene from Example 1A and 9.4 g (60 mmol) of 2-chlorophenylboric acid were dissolved in 170 mL of toluene under nitrogen. Then, 0.1 g (0.5 mmol) of palladium acetate, 0.35 g (1 mmol) of 2-(dicyclohexylphosphino) biphenyl and 15 g of tripotassium phosphate were added, and the reaction mixture was heated to 80° C. At the end of the reaction, the reaction mixture was poured into 100 mL of ethyl acetate and the organic phase was extracted with dilute sodium hydroxide solution and then dried over magnesium sulfite. The solvent was distilled off in a rotary evaporator, and the residue was purified on silica gel with hexane/ethyl acetate (9:1).

The resulting product dissolved in 50 mL of ethanol was heated to 50° C. Then, 80 mL of a 2.9-molar ethanolic hydrochloric acid solution was added dropwise. The reaction mixture was cooled to 0° C. The precipitate was filtered off, washed twice with 20-mL portions of ethanol and then dried. This gave 9.35 g of 4-nitro-2'-chloro[1,1'-biphenyl]-3-ol.

$^1$H-NMR: (300 MHz DMSO-D6): δ=111.18 (s, 1H), 8.0 (d, 1), 7.62 (m, 1H), 7,48 (m,3H), 7.18 (d, 1H), 7.03 (dd, 1H)

B. Synthesis of 4-amino-2'-chloro[1,1'-biphenyl]-3-ol 9.9 g (40 mmol) of 4-nitro-2'[1,1'-biphenyl]-3-ol from step A was dissolved in 120 mL of ethanol and hydrogenated in the presence of 0.8 g of a palladium-activated carbon catalyst (10%) at 25° C. After the required amount of hydrogen had been absorbed, the catalyst was filtered off, and the solvent was distilled off in a rotary evaporator. This gave 8.1 g of 4-amino-2'-chloro[1,1'-biphenyl]-3-ol.

$^1$H-NMR (300 MHz, DMSO-D6): δ=10.6 (s, 1H), 7.50 (m, 3H), 7.38 (m, 1H), 7.24 (m, 2H), 7.12 (dd, 1H).

Examples 3 to 22 Hair Colorants

Hair colorant solutions of the following composition were prepared:

| | | |
|---|---|---|
| X g | of 4-aminobiphenyl-3-ol derivative of formula (I) (substance O1 or O2 as per Table 1) |
| U g | of developer E8 to E15 as per Table 2 |
| Y g | of coupler K11 to K35 as per Table 4 |
| Z g | of direct dye D1 to D3 as per Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the above colorant solution was mixed with 30 g of a 6% aqueous hydrogen peroxide solution. The mixture was then applied to bleached hair. After an exposure time of 30 minutes at 40° C., the hair was rinsed with water, washed with a commercial shampoo and dried. Table 6 summarizes the coloring results.

Examples 23 to 34 Hair Colorants

Dye carriers in cream form and having the following composition were prepared:

| | | |
|---|---|---|
| X g | of 4-aminobiphenyl-3-ol derivative of formula (I) (substance O1 or O2 as per Table 1) |
| U g | of developer E8 to E15 as per Table 2 |
| Y g | of coupler K11 to K35 as per Table 4 |
| Z g | of direct dye D1 to D3 as per Table 3 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100.0 g | water |

Just before use, 30 g of the above colorant cream was mixed with 30 g of a 6% hydrogen peroxide solution. The mixture was then applied to hair. After an exposure time of 30 minutes, the hair was rinsed with water, washed with a commercial shampoo and dried. Table 7 summarizes the coloring results.

Examples 35 to 42 Hair Colorants

Hair colorant solutions of the following composition were prepared

| | | |
|---|---|---|
| X g | of 4-aminobiphenyl-3-ol derivative of formula (I) (substance O1 or O2 as per Table 1) |
| Z g | of dye component W1 or W2 as per Table 5 |
| U g | of developer E8 to E15 as per Table 2 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the above colorant solution was mixed with 30 g of a 6% hydrogen peroxide solution. The mixture was then applied to bleached hair. After an exposure time of 30 minutes at 40° C., the hair was rinsed with water, washed with a commercial shampoo and dried. The following Table 8 summarizes the coloring results.

TABLE 1

| 4-Aminobiphenyl-3-ol Derivative of Formula (I) | |
|---|---|
| O1 | 4-amino-1,1'-biphenyl-3-ol |
| O2 | 4-amino-2-chloro[1,1'-biphenyl]-3-ol |

TABLE 2

| Developers | |
|---|---|
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E12 | 4-aminophenol |
| E13 | N,N-bis-(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| Direct Dyes | |
|---|---|
| D1 | 2,6-diamino-3-[(pyridin-3-yl)azo]pyridine |
| D2 | 6-chloro-2-ethylamino-4-nitrophenol |
| D3 | 2-amino-6-chloro-4-nitrophenol |

TABLE 4

| Couplers | |
|---|---|
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis-(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |

TABLE 4-continued

Couplers

| | |
|---|---|
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxybenzene.HCl |
| K35 | 3,4-methylenedioxyphenol |

TABLE 5

Dye Components

| | |
|---|---|
| W1 | 4-(2,5-diaminobenzylamino)aniline.HCl |
| W2 | 2-(3-aminophenyl)aminomethyl-1,4-diaminobenzene.HCl |

TABLE 6

Hair Colorants

| | Example No. | | | | |
|---|---|---|---|---|---|
| | 3 | 4 | 5 | 6 | 7 |
| Dyes | (Dye quantity in grams) | | | | |
| O1 | 0.30 | 0.03 | 0.05 | 0.03 | 0.02 |
| E10 | | | | 0.55 | |
| E11 | | 0.55 | | | |
| E12 | | | 0.55 | | |
| E14 | | | | | 0.55 |
| K31 | | | | 0.18 | 0.20 |
| K32 | | 0.22 | | | |
| K33 | | | 0.20 | | |
| K25 | | 0.30 | | 0.30 | 0.30 |
| K26 | | | 0.35 | | |
| Coloring result | bright yellow | red-brown | red-brown | red-brown | red-brown |

| | Example No. | | | |
|---|---|---|---|---|
| | 8 | 9 | 10 | 11 |
| Dyes | (Dye quantity in grams) | | | |
| O1 | 0.010 | 0.005 | | |
| O2 | | | 0.010 | 0.005 |
| E8 | 0.100 | 0.100 | 0.100 | 0.100 |
| E9 | 0.250 | | 0.250 | |
| E15 | | 0.250 | | 0.250 |
| K13 | 0.090 | 0.090 | 0.090 | 0.090 |
| K31 | 0.200 | | 0.200 | |
| K32 | | 0.200 | | 0.200 |
| K33 | | | | |
| K21 | 0.050 | | 0.050 | |
| K22 | | 0.050 | | 0.050 |
| Coloring result | blond | blond | blond | blond |

| | Example No. | | | | | |
|---|---|---|---|---|---|---|
| | 12 | 13 | 14 | 15 | 16 | 17 |
| Dyes | (Dye quantity in grams) | | | | | |
| O1 | 0.010 | 0.006 | 0.020 | 0.005 | 0.050 | 0.010 |
| E9 | | | | 0.096 | | 1.800 |
| E10 | 0.096 | 0.240 | 0.300 | 0.900 | 0.010 | 0.700 |
| K12 | | | | | 0.010 | |
| K18 | | | | | | 0.030 |
| K21 | | | | | 0.020 | 0.060 |
| K22 | 0.080 | 0.200 | 0.250 | 0.056 | | 0.580 |
| K25 | | | | | 0.030 | |
| K31 | | | 0.200 | | | 0.800 |
| K32 | | 0.030 | 0.050 | 0.316 | | |
| D5 | 0.018 | | | | | |
| D2 | | | | | 0.010 | |
| D3 | | 0.040 | 0.060 | 0.025 | | |

TABLE 6-continued

Hair Colorants

| Color shade | bright blond to copper-gold | copper-gold | bright copper colors | purple-brown | silver-blond | dark mahogany |
|---|---|---|---|---|---|---|

| | Example No. | | | | |
|---|---|---|---|---|---|
| | 18 | 19 | 20 | 21 | 22 |
| Dyes | (Dye quantity in grams) | | | | |
| O1 | 0.03 | | 0.15 | 0.15 | |
| O2 | | 0.03 | | | 0.30 |
| E14 | 0.05 | 0.05 | 0.10 | 0.10 | |
| E8 | | | 0.50 | 0.50 | |
| E10 | 0.60 | 0.60 | 0.05 | 0.05 | |
| K12 | | | 1.10 | 1.10 | |
| K17 | | | 1.10 | 1.10 | |
| K22 | 0.50 | 0.50 | | | |
| K23 | | | 0.60 | 0.60 | |
| K32 | 0.03 | 0.03 | | | |
| K36 | | 0.03 | | | |
| D1 | 0.25 | 0.25 | | | |
| D2 | | | 0.50 | 0.50 | |
| D3 | 0.15 | 0.15 | | | |
| Color shade | orange | orange | red-orange | red-orange | yellow |

TABLE 7

Hair Colorant

| | Example No. | | | | | |
|---|---|---|---|---|---|---|
| | 23 | 24 | 25 | 26 | 27 | 28 |
| Dyes | (Dye quantity in grams) | | | | | |
| O1 | 0.10 | 0.05 | 0.01 | | | |
| O2 | | | | 0.10 | 0.05 | 0.01 |
| E15 | 0.70 | 0.70 | 0.70 | 0.70 | 0.70 | 0.70 |
| K12 | 0.10 | 0.10 | 0.10 | 0.10 | 0.10 | 0.10 |
| K23 | 0.10 | 0.10 | 0.10 | 0.10 | 0.10 | 0.10 |
| K31 | 0.40 | 0.40 | 0.40 | 0.40 | 0.40 | 0.40 |
| D2 | 0.10 | 0.10 | 0.10 | 0.10 | 0.10 | 0.10 |
| Coloring result | brown | brown | brown | brown | brown | brown |

| | Example No. | | | | | |
|---|---|---|---|---|---|---|
| | 29 | 30 | 31 | 32 | 33 | 34 |
| Dyes | (Dye quantity in grams) | | | | | |
| O1 | 0.005 | 0.270 | 0.010 | | | |
| O2 | | | | 0.005 | 0.270 | 0.010 |
| E8 | 0.250 | | | 0.250 | | |
| E9 | | 1.710 | 0.020 | | 1.710 | 0.020 |
| E10 | 2.000 | 0.200 | 0.010 | 2.000 | 0.200 | 0.010 |
| K13 | | 0.100 | | | 0.100 | |
| K16 | | | 0.015 | | | 0.015 |
| K21 | | 0.800 | | | 0.800 | |
| K22 | 1.800 | | 0.250 | 1.800 | | 0.250 |
| K23 | | 0.200 | | | 0.200 | |
| K26 | | | 0.030 | | | 0.030 |
| K31 | 0.250 | 0.135 | 0.020 | 0.250 | 0.135 | 0.020 |
| D2 | | 0.010 | | | 0.010 | |
| Color shade | orange colors | chocolate brown | silver blond | orange colors | chocolate brown | silver blond |

TABLE 8

| Dyes | Example No. | | | | | | | |
|---|---|---|---|---|---|---|---|---|
| | 35 | 36 | 37 | 38 | 39 | 40 | 41 | 42 |
| | (Dye quantity in grams) | | | | | | | |
| 01 | 0.01 | 0.18 | 0.04 | 0.18 | 0.18 | 0.18 | 0.06 | 0.18 |
| E8 | | 0.12 | | 0.12 | | | | |
| E9 | | | 0.12 | | 0.15 | | | |
| E15 | | | | | | 0.13 | | |
| W1 | 0.90 | | | 0.38 | | 0.38 | 0.38 | 0.38 |
| W2 | | 0.37 | 0.05 | | 0.58 | | | |
| Color | deep blue | medium brown | medium blond | black-brown | brown | black-brown | medium brown | brown |

Unless otherwise indicated, all percentages given in the present patent application are by weight.

The invention claimed is:

1. A colorant for oxidative dyeing of keretin fibers, particularly human hair, based on a developer-coupler combination, said colorant containing at least one 4-aminobiphenyl-3-ol derivative of general formula (I) or a physiologically compatible, water-soluble salt thereof,

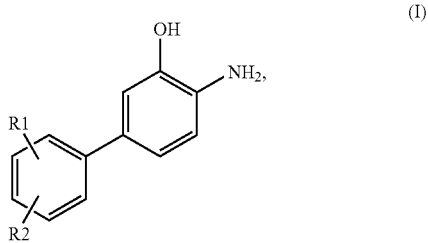

(I)

wherein R1 and R2 independently of each other denote hydrogen, a halogen atom, a cyano group, a hydroxyl group, $C_1$–$C_4$-alkoxy group, a $C_2$–$C_4$-hydroxyalkoxy group, a $C_1$–$C_6$-alkyl group, a nitro group, a trifluoromethyl group, a —C(O)H group, a —C(O)CH$_3$ group, a —C(O)CF$_3$ group, an —Si(CH$_3$)$_3$ group, a $C_1$–$C_6$-hydroxyalkyl group, or R1 and R2 together form an —O—CH$_2$—O— bridge.

2. The colorant as defined in claim 1, wherein the 4-aminobiphenyl-3-ol derivative of general formula (I) is selected from the group consisting of 4-aminobiphenyl-3-ol, 4-amino-2'-chlorobiphenyl-3-ol, 4-amino-2'-cyanobiphenyl-3-ol, 4-amino-2'-fluorobiphenyl-3-ol, 4-amino-2'-methylbiphenyl-3-ol, 4-amino-2-trifluoromethylbiphenyl-3-ol, 4-amino-3'-chlorobiphenyl-3-ol, 4-amino-3'-cyano-biphenyl-3-ol, 4-amino-3'-fluorobiphenyl-3-ol, 4-amino-3'-methybiphenyl-3-ol, 4-amino-3'-trifluoromethylbiphenyl-3-ol, 4-amino-4'-chlorobiphenyl-3-ol, 4-amino-4'-cyano-biphenyl-3-ol, 4-amino-4'-fluorobiphenyl-3-ol, 4-amino-4'-methylbiphenyl-3-ol, 4-amino-4-trifluoromethylbiphenyl-3-ol, 4-amino-2',3'-dichlorobiphenyl-3-ol, 4-amino-2'-chloro-3'-fluoro-biphenyl-3-ol, 4-amino-2'-chloro-3'-methylbiphenyl-3-ol, 4-amino-2'-chloro-5'-chlorobiphenyl-3-ol, 4-amino-2'-chloro-5'-fluorobiphenyl-3-ol, 4-amino-2'-chloro-5'-methylbiphenyl-3-ol, 4-amino-2,6'-dichlorobiphenyl-3-ol, 4-amino-2'-chloro-6'-fluoro-biphenyl-3-ol, 4-amino-2'chloro-6'methyl-biphenyl-3-ol, 4-amino-2'-fluoro-3'-chloro-biphenyl-3-ol, 4-amino-2'-fluoro-3-fluoro-biphenyl-3-ol, 4-amino-2'-fluoro-3'-methyl-biphenyl-3-ol, 4-amino-2'-fluoro-5'-chloro-biphenyl-3-ol, 4-amino-2',5'-difluoro-biphenyl-3-ol, 4-amino-2'-fluoro-5'-methylbiphenyl-3-ol, 4-amino-2'-fluoro-6'-chloro-biphenyl-3-ol, 4-amino-2',6'-difluorobiphenyl-3-ol, 4-amino-2'-fluoro-6'-methyl-biphenyl-3-ol, 4-amino-2'-methyl-3'-chlorobiphenyl-3-ol, 4-amino-2'-methyl-3'-fluoro-biphenyl-3-ol, 4-amino-2',3'-dimethylbiphenyl-3-ol, 4-amino-2'-methyl-5'-chlorobiphenyl-3-ol, 4-amino-2'-methyl-5'-fluorobiphenyl-3-ol, 4-amino-2',5'-dimethylbiphenyl-3-ol, 4-amino-2'-methyl-6'-chlorobiphenyl-3-ol, 4-amino-2'-methyl-6'-fluorobiphenyl-3-ol, 4-amino-2',6'-dimethyl-biphenyl-3-ol, 4-amino-3'-chloro-5'-chlorobiphenyl-3-ol, 4-amino 3'-chloro 5'-fluorobiphenyl-3-ol, 4-amino-3'-chloro-5'-methylbiphenyl-3-ol, 4-amino-3'-fluoro-5'-chlorobiphenyl-3-ol, 4-amino-3',5'-difluorobiphenyl-3-ol, 4-amino-3'-fluoro-5'-methylbiphenyl-3-ol, 4-amino-3'-methyl-5'-chlorobiphenyl-3-ol, 4-amino-3'-methyl-5'-fluorobiphenyl-3-ol, 4-amino-3',5-dimethyl-biphenyl-3-ol, 4-amino-3',4'-dichloro-biphenyl-3-ol, 4-amino-3'-chloro-4'-fluorobiphenyl-3-ol, 4-amino-3'-chloro-4'-methylbiphenyl-3-ol, 4-amino-4',6'-dichlorobiphenyl-3-ol, 4-amino-4'-chloro-6'-fluorobiphenyl-3-ol, 4-amino-4'-chloro-6'-methylbiphenyl-3-ol, 4-amino-3'-fluoro-4'-chlorobiphenyl-3-ol, 4-amino-3',4'-difluorobiphenyl-3-ol, 4-amino-3'-fluoro-4'-methyl-biphenyl-3-ol, 4-amino-4'-fluoro-6'-chlorobiphenyl-3-ol, 4-amino-4',6'-difluorobiphenyl-3-ol, 4-amino-4'-fluoro-6'-methylbiphenyl-3-ol, 4-amino-3'-methyl-4'-chlorobiphenyl-3-ol, 4-amino-3'-methyl-4'-fluorobiphenyl-3-ol, 4-amino-3',4'-dimethylbiphenyl-3-ol, 4-amino-4'-methyl-6'-chlorobiphenyl-3-ol, 4-amino-4'-methyl-6'-fluorobiphenyl-3-ol, 4-amino-4', 6'-dimethylbiphenyl-3-ol, and 2-amino-5-benzo[1,3]dioxo-5-ylphenol.

3. The colorant as defined in claim 1, wherein in the formula (I) (i) R1 denotes hydrogen and/or (ii) R2 denotes hydrogen, a methyl group, a trifluoromethyl group, a fluorine atom, or a chlorine atom.

4. The colorant as defined in claim 1, wherein the 4-aminobiphenyl-3-ol derivative of general formula (I) is selected from the group consisting of 4-aminobiphenyl-3-ol, 4-amino-2'-chlorobiphenyl-3-ol, 4-amino-3'-chlorobiphenyl-3-ol, 4-amino-4'-chlorobiphenyl-3-ol, 4-amino-2'-fluorobiphenyl-3-ol, 4-amino-3'-fluorobiphenyl-3-ol, 4-amino-4-fluorobiphenyl-3-ol, and 4-amino-4'-methyl-biphenyl-3-ol.

5. The colorant as defined is claim 1, containing the 4-amino biphenyl-3-ol derivative of general formula (I) in an amount from 0.001 to 5 weight percent.

6. The colorant as defined is claim 1, having a pH of 6.5 to 11.5.

7. The colorant as defined in claim 1, containing at least one dye selected from the group consisting of developers, couplers, direct dyes, and other dye components.

8. A 4-Aminobiphenyl-3-ol derivative of general formula (I) or a physiologically compatible, water-soluble salt thereof:

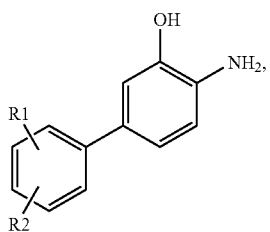

wherein R1 and R2 independently of each other denote hydrogen, a halogen atom, a cyano group, a hydroxyl group, a $C_1$–$C_4$-alkoxy group, a $C_2$–$C_4$-hydroxyalkoxy group, a $C_1$–$C_6$-alkyl group, a nitro group, a triflurormethyl group, a —C(O)H group, a —C(O)CH$_3$ group, a —C(O)CF$_3$ group, an —Si(CH$_3$)$_3$ group, a $C_1$–$C_6$hydroxyalkyl group, or $R_1$ and $R_2$ together from an —O—CH$_2$—O— bridge.

9. The compound as defined in claim 8, wherein in the formula (I) (i) $R_1$ denotes hydrogen and/or (ii) $R_2$ denotes hydrogen, a methyl group, a trifluoromethyl group, a fluorine atom, or a chlorine atom.

* * * * *